United States Patent [19]

Tarroux et al.

[11] Patent Number: 4,767,855

[45] Date of Patent: Aug. 30, 1988

[54] PROCESS FOR THE PREPARATION OF VINCRISTINE

[75] Inventors: Roger Tarroux, Castres; Jacques Fahy, Labruguiere; Philippe Hatinguais, Castres, all of France

[73] Assignee: P. F. Medicament, Paris, France

[21] Appl. No.: 869,433

[22] Filed: Jun. 2, 1986

[30] Foreign Application Priority Data

Jun. 3, 1985 [FR] France .................................. 85 08333

[51] Int. Cl.$^4$ .......................................... C07D 519/04
[52] U.S. Cl. .................................................... 540/478
[58] Field of Search ......................................... 540/478

[56] References Cited

U.S. PATENT DOCUMENTS 3,899,493  8/1975  Jovanovics et al. ................ 540/478
4,375,432  3/1983  Conrad ................................ 540/478
4,659,816  4/1987  Szántay et al. ..................... 540/478

FOREIGN PATENT DOCUMENTS 0117861  9/1984  European Pat. Off. ........... 540/478
1551054  8/1979  United Kingdom .

Primary Examiner—Donald G. Daus
Assistant Examiner—Diana G. Rivers
Attorney, Agent, or Firm—Dressler, Goldsmith, Shore, Sutker & Milnamow, Ltd.

[57] ABSTRACT

The present invention relates to a process for the preparation of vincristine.

The process for the semisynthesis of vincristine according to the present invention comprises oxidizing vinblastine or its salts with chromic acid or its salts, in ethyl acetate at a low temperature.

7 Claims, No Drawings

PROCESS FOR THE PREPARATION OF VINCRISTINE

The present invention relates to a particularly efficient process for the preparation of vincristine.

The cytostatic alkaloids of Vinca rosea L. Catharanthus roseus G. Don) are now well-known and particularly useful anticancer agents. In view of the small quantity of vincristine present in Catharanthus, chemists have proposed a fairly large number of methods for its preparation. Thus, Patent document FR-A-No. 2 296 418 describes the synthesis of vincristine by coupling catharanthine and vindoline. Other laboratories have converted vinblastine to vincristine by oxidation under very strict, controlled conditions.

Patent documents FR-A- No. 2 210 393 and U.S. Pat. No. 3,899,493 perform the oxidation with chromic acid at $-30$, $-90°$ C. in an acetone/acetic acid mixture or at $-55°$ C. in chloroform/acetic acid.

Patent document U.S. Pat. No. 4,375,432 also uses chromic oxide in an acid medium at $-65°$ C., $-50°$ C., but in a THF/ acetic acid mixture. Moreover, Patent document EP-A-No. 37 289 claims oxidation with a mixture of ferrous salt, hydrogen peroxide and perchlorate in acetonitrile. Patent document ZA-A-No. 82 08939 describes a process involving chromic acid and an ether/chloroform mixture.

Patent document HU-A-No. 23 638 proposes ditert.-butyl chromate in pelargonic acid and, finally, Patent document EP-A-No. 117 861 effects the vinblastine/vincristine conversion by oxidation with potassium permanganate in an acetic acid medium. It is clear that these dimeric alkaloids are precious substances on account of their small quantity in the plant raw materials, and consequently that high-performance processes for their synthesis or semisynthesis are extremely valuable.

With this in mind, we carried out a thorough study of the oxidation in a variety of solvents compatible with the solubilities of the reactants and with a low temperature.

It is curious to observe the great importance of the solvent used, since the majority of them do not enable vincristine to be obtained correctly: methanol, dimethylformamide, chloroform, toluene, benzene, ethylene glycol monoethyl ether, ethylene glycol dimethyl ether and dimethyl sulfoxide give practically zero yields. Methyl acetate, acetonitrile, dioxane, butyl acetate, ethyl formate, acetone, methyl isobutyl ketone and methyl ethyl ketone give mediocre yields. We confirmed the good yields obtained in THF (Patent document U.S. Pat. No. 4,375,432), but we found separation difficulties due to stable emulsions when the reaction medium was extracted with methylene chloride.

Totally surprisingly, we discovered that ethyl acetate is an excellent solvent for the oxidation of vinblastine to vincristine, compared with all those already recommended in the prior art.

The oxidizing agent used is chromic acid or its salts and the reaction is carried out at a temperature of between $-83°$ C. and $-25°$ C.

The process for the semisynthesis of vincristine which is thus used according to the invention affords the following advantages:

high yield (80-90%)

non-toxicity (compared with formic acid, chlorinated or aromatic solvents, acetonitrile)

does not form peroxides (compared with ether, THF)

relatively low flammability (compared with ether, THF)

permits a large temperature range starting from $-83°$ C. (compared with acetic acid, acetonitrile or pelargonic acid), and facilitates the final separation of the vincristine after the reaction mixture has been rendered alkaline, because of the immiscibility with water (compared with acetic acid, acetic anhydride, acetone, formic acid, THF, acetonitrile).

TYPICAL NON-LIMITING EXAMPLE ILLUSTRATING THE SEMISYNTHESIS ACCORDING TO THE INVENTION 20 g of vinblastine base are solubilized in 2 liters of ethyl acetate and 40 ml of acetic acid. The temperature is brought down to $-70$, $-60°$ C. and a solution of 30 g of sodium bichromate in 130 ml of water and 8 ml of sulfuric acid is added slowly, with vigorous stirring, the temperature of the reaction medium being kept at $-70$, $-60°$ C.

Stirring is continued for 2 hours.

200 ml of 10% aqueous ammonia are added slowly so as to neutralize the reaction medium without an excessive rise in temperature.

The ethyl acetate containing the crude vincristine base is decanted. A second extraction is carried out with 1 liter of the same solvent. The combined organic phases are washed and evaporated in vacuo at 40°–45°C.

The residue of crude vincristine is solubilized in 100 ml of toluene and the solution is purified by chromatography on a column of Merck ® 60 mesh silica with a toluene/methanol elution gradient (3 to 20% of methanol).

The vincristine is repurified by crystallization from methanol, after which the sulfate or other salt is obtained by the conventional processes of salt formation with a therapeutically acceptable acid. Yield: 70–80%

This same oxidation technique was successfully applied to the related dimers containing a methylated $N_1$ nitrogen atom, i.e., for example, 4-deoxyleurosidine or leurosine.

What is claimed is:

1. A process for the semisynthesis of vincristine, which comprises oxidizing vinblastine or its salts with chromic acid or its salts, in a reaction medium of ethyl acetate at a low temperature.

2. The process as claimed in claim 1, wherein acetic acid is added to the reaction medium.

3. The process as claimed in claim 2, wherein the reaction is carried out at a temperature of between $-83°$ C. and $-25°$ C.

4. The process as claimed in claim 3, wherein a vincristine base is obtained directly by neutralization of the reaction medium to extract the crude vincristine base therefrom into the ethyl acetate and decanting the ethyl acetate containing the crude vincristine base.

5. The process as claimed in claim 4, wherein the crude vincristine is purified by chromatography on silica using a toluene/methanol elution gradient.

6. The process as claimed in claim 5, wherein the purified vincristine is repurified by crystallization from methanol.

7. The process as claimed in claim 6, wherein the vincristine is converted to a salt with a therapeutically acceptable acid.

* * * * *